United States Patent [19]

Rosenthal et al.

[11] Patent Number: 5,719,035
[45] Date of Patent: *Feb. 17, 1998

[54] ASSAY FOR ENZYME ACTIVITY FROM A RED BLOOD SAMPLE USING A DIRECT MICROFLUOROMETRIC ASSAY

[75] Inventors: Murray A. Rosenthal, Copley; Ronald A. Simkins, Wooster; Ranjan Akhaury, Akron, all of Ohio

[73] Assignee: Isolab, Inc., Norton, Ohio

[*] Notice: The term of this patent shall not extend beyond the expiration date of Pat. No. 5,538,857.

[21] Appl. No.: 643,539

[22] Filed: May 6, 1996

Related U.S. Application Data

[62] Division of Ser. No. 252,595, Jun. 1, 1994, Pat. No. 5,538,857.

[51] Int. Cl.$^6$ ............................................. C12Q 1/48
[52] U.S. Cl. .................. 435/15; 435/4; 435/7.72; 435/7.4; 424/94.1; 424/529
[58] Field of Search ............... 435/4, 7.4, 7.72, 435/968, 15; 436/68, 164, 172; 530/380, 385; 424/94.1, 529, 533

[56] References Cited

U.S. PATENT DOCUMENTS

| | | | |
|---|---|---|---|
| 3,616,254 | 10/1971 | Beutler | 195/103.5 |
| 5,173,407 | 12/1992 | Uemura et al. | 435/15 |
| 5,213,966 | 5/1993 | Vuorinen et al. | 435/14 |
| 5,240,571 | 8/1993 | Heineman et al. | 204/153.12 |
| 5,538,857 | 7/1996 | Rosenthal et al. | 435/15 |

OTHER PUBLICATIONS

Yamaguchi, Akihiro *Technical Manual on Screening for Inborn Errors of Metabolism.* Sapporo City Institute of Public Health, 1991.

Pitkanen, Kahja and Tuuminen, Tamara "A quantitative fluorometric micromethod used for the neonatal screening of biotinidase deficiency in Finland" *Screening*, 1 (1992) 185–194.

Anderson et al. "A Specific Enzymatic Assay for the Diagnosis of Congenital Galactosemia". *J. Lab & Clin. Med.*, Sep., 1957, pp. 469–477.

Beutler, Ernest and Baluda, Maryellen C. "A simple spot screening test for galactosemia". *J. Lab & Clin. Med.*, Jul. 1996, pp. 137–141.

Beutler, Ernest and Baluda, Maryellen and Donnell, George N. "A new method for the detection of galactosemia and its carrier state". *J. Lab & Clin. Med.*, Oct., 1964, pp. 694–705.

Pesce et al. "Enzymatic Micromethod for Measuring Galactose-1-phosphate Uridylyltransferase Activity in Human Erythrocytes". *Clinical Chemistry*, vol. 23, No. 9, 1977, pp. 1711–1717.

Weissbecker et al. "An Automated Procedure for Measuring Biotinidase Activity in Serum". *Clinical Chemistry*, vol. 23, No. 5, 1989, pp. 831–833.

Lawler et al. "Newborn screening for biotinidase deficiency: pilot study and follow–up of identified cases". *Screening*. 1 (1992) 37–47.

Heard et al. "A Screening Method for Biotinidase Deficiency in Newborns". *Clinical Chemistry*, vol. 30, No. 1, 1984, pp. 125–127.

Wastell, H. and Dale, G. and Bartlett, K. "A Sensitive Fluorimetric Rate Assay for Biotinidase Using a New Derivative of Biotin. Biotinyl–6–aminoquinoline". *Analytical Biochemistry*, 140, 69–73 (1984).

Ebrahim, H. and Dakshinamurti, K. "A Fluorometric Assay for Biotinidase". *Analytical Biochemistry*, 154, 282–286 (1986).

Pettit, D.A. Dove and Wolf, Barry "Quantitative Colorimetric Assay of Biotinidase Activity" *Techniques in Diagnostic Human Biochemical Genetics: A Laboratory Manual*, 1991, pp. 561–565.

Beutler E: Galactosemia: screening and diagnosis. *Clin. Biochem.* 24:293 (1991).

Sigma Diagnostics: Galatose–1–phosphate uridyl transferase deficiency. Procedure No. 195 (1985).

Berry HK: Reagent that restores galactose–1–phosphate uridyltransferase activity in dry blood spots. *Clin. Chem.* 33:1471 (1987).

Hochella NJ and Hill JB: Fluorometric screening procedure for galactosemia utilizing the autoanalyzer. *Clin. Chem.* 15:949 (1969).

Greenberg CR, Dilling LA, Thompson R, Ford JD, Seargeant LE, Haworth JC: Newborn screening for galactosemia: a new method used in Manitoba. *Pediatrics* 84:331 (1989).

Yamaguchi A, Fukushi M, Mizushima Y, Shimizu Y, Takasugi N, Arashima S, Ohyanagi K: Microassay for screening newborns for galactosemia with the use of a fluorometric microplate reader. *Clin. Chem.* 35:1962 (1989).

Frazier DM, Clemons EH, Kirkman HN: Minimizing false positive diagnoses in newborn screening for galactosemia. *Biochem. Med. Metabol. Biol.* 48:199 (1992).

Wolf, et al.: Clinical Findings in Four Children With Biotinidase Deficiency Detected Through a Statewide Neonatal Screening Program. *The New England Journal of Medicine*, 313:1:16 (1985).

(List continued on next page.)

*Primary Examiner*—John Kight
*Assistant Examiner*—Dameron Jones
*Attorney, Agent, or Firm*—Standley & Gilcrest

[57] ABSTRACT

The present invention is a method for assaying enzyme activity in a red blood sample. The method comprises these steps: (a) placing the following in a sample well: (1) a red blood sample containing an enzyme, (2) a substrate or substrates for the enzyme, (3) water, and (4) a buffer; (b) incubating the contents of the sample well for sufficient time and at sufficient temperature to allow for the formation of a fluorescent enzyme product should the enzyme be present in said red blood sample; (c) precipitating the hemoglobin; and (d) measuring the fluorescence of any fluorescent enzyme product formed in the sample well, directly from that sample well. The method of the invention may be used for assaying the activity of an enzyme, such as galactose-1-phosphate uridyl transferase (GALT) or biotinidase, in a red blood sample.

20 Claims, 1 Drawing Sheet

Wolf, et al: Phenotypic variation in biotinidase deficiency. *The Journal of Pediatrics*, 103:2:233 (1983).

Wolf, et al: Screening for Biotinidase Deficiency in Newborns: Worldwide Experience. *Pediatrics*, 85:4:512 (1989).

Lawler, et al: Newborn screening for biotinidase deficiency: pilot study and follow-up of identified cases. *Screening*, 1 (1992) 37–47.

Dunkel, et al: Prospective Ascertainment of Complete and Partial Serum Biotinidase Deficiency in the Newborn. *J. Inher. Metab. Dis.* 12 (1989) 131–138.

Wolf, et al: The Metabolic Basis of Inherited Disease Disorders of Biotin Metabolism, Chapter 83, 1989.

Heard, et al: A Screening Method for Biotinidase Deficiency in Newborns, *Clin. Chem.* 30/1, 125–127 (1984).

Pettit, et al.: Quantitative Colorimetric Assay of Biotinidase Activity, *Techniques in Diagnostic Human Biochemical Genetics: A Laboratory Manual*, 31:561–565 (1989).

Hayakawa, et al.: Determination of biotinidase activity by liquid chromatography with fluorimetric detection, *Journal of Chromatography*, 383 (1986) 148–152.

Weiner, et al.: A Bioassay for Determining Biotinidase Activity and for Discriminating Biocytin from Biotin using Holocarboxylase Synthetase–deficient Cultured Fibroblasts, *J. Inher. Metab. Dis.* 8 Supp. 2 (1985) 101–102.

Thoma, et al: The Enzymatic Degradation of Soluble Round Biotin, pp. 569–679 (1954).

Wright, et al: Biocytinase, an Enzyme Concerned with Hydrolytic Cleavage of Biocytin, p. 335 (1954).

Baker, et al: Plasma Biotinidase Assay Using the Protozoan Ochromonas Danica, *Nutrition Reports International*, 39:2:243–51 (Feb. 1989).

Thuy, et al: Determination of biotinidase activity in human plasma using $[^{14}C]$–biocytin as substrate, *Ann. NY Acad. Sci.*, 447:434 (1985).

Lagrou, et al: Simplified Assay of Galactose–1–phosphate Uridyltransferase, *Clin. Chem.*, 37:12:2157–2158 (Dec. 1991).

Catomeris, et al: An Improved Kinetic Fluorometric Enzymic Coupled Assay For The Determination Of Galactose–1–Phosphate Uridylyl Transferase In Erythrocytes, *Chemical Abstracts*, 110:311, Ref. No. 3342p, (1989). *Microchemical Journal*, 38:251–263 (1988).

Beutler, et al: Falsely Normal Value In Fluorometric Transferase Screening Of Galactosemic Blood. A Cautionary Note, *Am. J. Clin. Pathol.*, 76:6:841–842 (1981).

Frazier, et al: *Biological Abstracts*, 95:7:725–726, Ref. No. 75572 (1992).

ASSAY FOR ENZYME ACTIVITY FROM A RED BLOOD SAMPLE USING A DIRECT MICROFLUOROMETRIC ASSAY

This application is a divisional of application Ser. No. 08/252,595, now U.S. Pat. No. 5,538,857 filed Jun. 1, 1994.

TECHNICAL FIELD

This invention relates to methods of providing an indication of the mount of an enzyme (such as galactose-1-phosphate uridyl transferase activity (GALT) or biotinidase) in blood samples.

GALT activity is used in screening newborns for galactosemia. The method involves an adaptation of the Beutler and Baluda GALT assay to a microtiter plate assay using fluorescence readout. It has also been found that non-human blood, such as horse blood, makes a good enzyme deficient control for the GALT assay.

This invention also relates to a method of providing a quantitative determination of biotinidase activity in blood samples. This method involves an adaptation of the Pitkanen and Tuuminen quantitative fluorometric assay for biotinidase deficiency.

BACKGROUND ART

The following abbreviations will be used in this disclosure:

| | |
|---|---|
| GAL | Galactose |
| GALT | Galactose-1-Phosphate Uridyl Transferase |
| GAL-1-P | Galactose-1-Phosphate |
| UDPG | Uridine Diphosphoglucose |
| UDP-GAL | Uridine Diphosphogalactose |
| G-1-P | Glucose-1-Phosphate |
| PGM | Phosphoglucomutase |
| G-6-P | Glucose-6-Phosphate |
| NADP | Nicotinamide Adenine Dinucleotide Phosphate |
| NADPH | Nicotinamide Adenine Dinucleotide, Reduced |
| G-6-PDH | Glucose-6-Phosphate Dehydrogenase |
| 6-PGA | 6-Phosphogluconate |
| 6-PGD | 6-Phosphogluconate Dehydrogenase |
| R-5-P | Ribulose-5-Phosphate |
| TRIS | Tris(hydroxyethyl)aminomethane |
| EDTA | Ethylenediaminetetraacetic Acid |
| EtOH | Ethanol |
| MeOH | Methanol |
| DTT | Dithiothreitol |

The incidence of galactosemia is about 1 in 80,000 births in the U.S. If the disease is detected in the first few days of life, a newborn can be placed on special galactose-free diets to prevent the severe symptoms of the disease. Galactose is generally derived from lactose, which is the main carbohydrate in milk. When galactosemia is not detected in the first few days of life, it may cause liver damage, cataracts, mental retardation and, occasionally, death.

Accordingly, it is very desirable to test reliably for galactosemia in newborns; enabling the appropriate treatment measures to be timely taken.

There are two commonly used methods to detect galactosemia in newborns. One way is to measure the metabolites (GAL and GAL-1-P), which accumulate in the neonate's blood. This accumulation can occur only after dietary exposure of the infant to milk. Levels of the metabolites increase and remain high due to enzyme deficiency. An alternative method measures galactose-1-phosphate uridyl transferase (E.C. 2.7.7.12; GALT) activity, the most common enzyme deficiency in galactosemia. The following Table 1 compares and contrasts these two methods:

TABLE 1

| PROPERTY | TOTAL GALACTOSE ASSAY | GALT ASSAY |
|---|---|---|
| ANALYTE DETECTS | GAL & GAL-1-P ALL FORMS OF GALACTOSEMIA | GALT ACTIVITY ONLY GALT DEFICIENCY |
| PATIENT REQUIREMENTS | MUST BE EXPOSED TO GAL IN DIET | ASSAY REQUIRES THREE ENZYMES FROM SAMPLE |
| SAMPLE STABILITY | GOOD | ENZYME(S) DEGRADE IN HEAT DURING TRANSPORT |
| UNITS | mg/dL GAL | $\mu mol\ hour^{-1}\ mL^{-1}$ or % activity of a high control |

There are three enzymes whose deficiency leads to galactosemia: GALT, galactokinase, and UDPG galactose-4-epimerase. Classic galactosemia (GALT deficiency) is the most common. GALT deficiency is an inborn error of metabolism transmitted through an autosomal recessive gene. Untreated galactokinase-deficient patients suffer from cataracts, but other debilitating symptoms do not occur. The epimermase deficiency is quite rare and, in most cases, there are few clinical symptoms associated with epimerase deficiency. For a review of screening and diagnosis of galactosemia, see Beutler (1991).

In 1966, Beutler and Baluda reported a spot screening test for GALT deficiency. In that procedure, NADP is reduced to NADPH as a result of a series of enzymatic reactions. The assay is very simple. Sample is mixed with reagent and allowed to incubate for a certain period of time. Drops of the reaction mixture are removed and spotted onto filter paper. NADPH fluorescence is then detected using a black light (long-wave UV light). If GALT activity is not present in a blood sample, NADP is not reduced to NADPH and no fluorescence results. In this assay, GALT catalyses the reaction:

The above reaction is coupled to the following enzyme system to yield a fluorescent NADPH product:

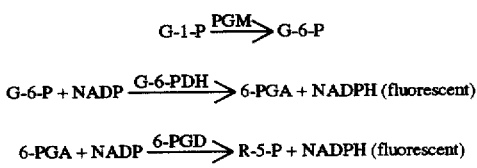

In the Beutler and Baluda procedure, a reaction mixture containing GAL-1-P, UDPG, and NADP is mixed with a blood sample and incubated at 37° C. Since GALT is located in the red blood cell, whole blood or a dried blood spot is generally the sample of choice. Drops from the reaction mixture are spotted onto filter paper at time zero and at various intervals during the incubation. The spots are then visualized under UV light. Fluorescence indicates the presence of GALT activity. The fluorescence will range from bright for normal blood to no fluorescence for GALT deficient samples. If the blood is from a heterozygote for GALT deficiency, a subdued fluorescence results. Three enzymes required for the reaction are provided by the patient's blood: PGM, G-6-PDH and 6-PGD. This paper-spot assay has been commercialized by Sigma Diagnostics, St. Louis, Mo. (Procedure No. 195).

This assay has two major flaws. The first is that this fluorescent spot test may miss samples that are galactose kinase deficient. The second flaw is that GALT is unstable to heating, and samples stored at high temperatures may give false positive results. It has recently been proposed (Berry 1987) that this problem can be largely overcome by the addition of DTT to the reaction mixture. The Beutler and Baluda assay has also been adapted to an autoanalyzer (Hochella and Hill 1969) for screening samples collected as dried blood spots on filter paper. A reagent similar to the Beutler and Beluda reagent is added to eluted blood samples. The samples are loaded on an autoanalyzer and measured twice (at time zero and an hour later). The difference in fluorescence intensity of the two readings is used as evidence of GALT activity. The authors emphasized that their assay could not give results expressed in international enzyme units, but was rather designed for a screening method to give a yes/no answer.

Methods which measure the NADPH product optically have also been reported. A kinetic micro-spectrophotometric assay of whole blood was done in an LKB Reaction Rate Analyzer (Pesce et al. 1977). In this assay a modified Beutler reagent is mixed with whole blood and the rate of NADPH formation is measured spectrophotometrically. Actual enzyme units can be calculated after hemoglobin concentration measurement.

The GALT assay has also been used to confirm the results of total (GAL plus GAL-1-P) galactose assays (Greenberg et al. 1989).

The use of microtiter plates and fluorescent readout has been recently described (Yamaguchi et al. 1989) in which total galactose (GAL plus GAL-1-P) was measured in blood dried on filter paper. A punched-out spot was first extracted with a methanol:acetone:water mixture, during which hemoglobin and other proteins were denatured. Water was then added and the extract transferred to an assay plate where a galactose dehydrogenase enzyme reagent converted galactose and NAD to products. The NADH product concentration, which is proportional to the original galactose concentration in the sample, was measured fluorometrically.

A manual fluorometric assay for GALT activity has also been reported (Frazier, Clemons, and Kirkman 1992). A dried blood spot on filter paper was mixed with a modified Beutler reagent and incubated for various amounts of time; after which a portion of the sample-reagent mixture was transferred to a holding reagent, which stopped the reaction. A Turner fluorometer was used to measure fluorescence.

Biotinidase deficiency, also termed late-onset or juvenile multiple-carboxylase deficiency, is a rare genetic disease inherited as an autosomal recessive trait (Pettit and Wolf, 1991; Pitkanen and Tuuminen, 1992). Individuals having biotinidase deficiency exhibit a variety of symptoms, such as seizures, hypotonia, alopecia, skin rash, hearing loss, developmental delay, keto-lactic acidosis, and organic aciduria (Wolf et al., 1985), making it difficult to diagnose the disease clinically. Biotinidase deficiency can be of three types: (i) complete or profound biotinidase deficiency (less than 10% of mean normal adult activity), (ii) partial biotinidase deficiency (10–30% of mean adult activity), and (iii) transient biotinidase deficiency (little or no activity in the original newborn blood specimen and normal activity in a requested repeat filter-paper specimen). Pharmacological doses of oral biotin (10 mg/day) may alleviate symptoms and, if initiated early, may prevent them (Wolf et al., 1983; Wolf and Heard, 1989).

The incidence of biotinidase deficiency varies widely. The frequency of 1:33,000 for profound biotinidase deficiency in Massachusetts (Lawler et al., 1992) is similar to the incidence of 1:54,000 in Quebec (Dunkel et al., 1989). The mean frequency for profound biotinidase deficiency from worldwide screening experience is 1:137,000; but there is a wide range among these screening programs, varying from 1:33,000 in New Zealand to <1:500,000 in Illinois (Wolf and Heard, 1990).

Biotinidase deficiency can be identified in newborn infants by a simple and inexpensive screening test which was first demonstrated by Wolf and his group (Wolf et al., 1985) and repeated by the screening program in Quebec (Dunkel et. al., 1989) and a number of others (Wolf and Heard, 1990). The screening test is easily accommodated in newborn screening programs.

Biotinidase activity can be determined using a modification of the colorimetric assay described by Knappe et al. (1963) which measures the release of p-aminobenzoate (p-ABA) from the artificial substrate, biotinyl-p-aminobenzoic acid (B-pABA), an analogue of biocytin. Further modification of this assay has enabled quantitative and qualitative determination of biotinidase activity in whole-blood filter-paper spots (Heard et al., 1984; Dove Pettit et al., 1989). The main drawback of the colorimetric assay is that it requires visual inspection, which may be subjective. The quantitative determination of biotinidase activity requires a serum or plasma as the sample, often not available where only blood spots are available or practical.

Another method is to separate p-ABA from B-pABA by high performance liquid chromatography in which p-ABA concentration is determined fluorometrically (Hayakawa and Oizumi, 1986). An advantage of this method is that p-ABA can be distinguished from sulfonamides and other interferents. However, this method is not practical for clinical screening purposes.

Biocytin, the natural substrate of biotinidase, is used in several methods. One method detects the activation and increase of propionyl-CoA carboxylase activity in holocarboxylase synthetase-deficient fibroblasts by measuring the biotin that is liberated from biocytin by biotinidase (Weiner et al., 1985). Other methods observe the growth of biotin-dependent bacteria or protozoa from the biotin that is liberated from biocytin (Thoma and Peterson, 1954; Wright et al., 1954; Baker et al., 1989). An additional method is a radioassay in which liberated [$^{14}$C]biotin is separated from [$^{14}$C]biocytin by anion-exchange chromatography (Thuy et al., 1985). These methods are laborious and require reagents which are not readily available and may need to be synthesized, making these assays impractical for use in clinical or diagnostic settings.

One microplate-based fluorometric assay measures the release of 6-aminoquinoline from the artificial substrate biotinyl-6-aminoquinoline (Wastell et al., 1984; Pitkanen and Tuuminen, 1992). The disadvantage of this method is that it utilizes serum or plasma. Another fluorometric assay uses biocytin and measures the release of lysine, which complexes with 1,2-diacetylbenzene to give a fluorescent product. The drawbacks of this method are that it uses serum that must be dialyzed extensively, and that it is not microplate-based.

The microplate-based fluorometric assay seems the most promising for screening due to its low cost and robustness. However, the main drawback is that it requires serum as a sample.

With the foregoing background in mind, it is desirable to be able to perform an enzyme assay (such as a GALT or biotinidase assay) in a single analysis vessel, and to have an assay protocol which can be used with conveniently handled samples. It is also advantageous to be able to analyze a sample without having to transfer it from one vessel to another prior to analysis.

It is also desirable to be able to perform a quantitative enzyme assay (such as a GALT or biotinidase assay) using a single reading by the operator.

Problems associated with enzyme assays are errors where increases in enzyme activity occur due to more or less sample. Accordingly, it is beneficial to produce an assay protocol capable of balancing such effects.

Because enzyme deficient patients are so rare, it is difficult to obtain human blood for making control materials. Accordingly, it is desirable to be able to use commonly available substances which can be used to make appropriately precise enzyme-deficient controls.

Although described in the context of an enzyme assay for GALT or biotinidase, the present invention may be applied to solve the problems associated with other enzyme assays conducted in the presence of hemoglobin. These include other enzymes associated with the cellular and/or serum portions of a blood sample.

In view of the present disclosure and/or through the practice of the invention itself, other efficiencies, benefits and advantages, and/or the solution to other problems may become apparent to one of ordinary skill in the art.

SUMMARY OF INVENTION

The present invention is a method for assaying the activity of an enzyme, such as galactose-1-phosphate uridyl transferase (GALT) or biotinidase, in a red blood sample. As used herein, the term "red blood sample" shall be construed to include any hemoglobin-containing blood or blood product, such as whole blood, washed red blood cells, a hemolysate made from red blood cells, and a dried whole blood sample on a physical support, the latter of which is preferred.

The present invention, in broadest terms, is a method for assaying enzyme activity in a red blood sample. The method comprises these steps: (a) placing the following in a sample well: (1) a red blood sample containing an enzyme, (2) a substrate or substrates for the enzyme, (3) water, and (4) a buffer; (b) incubating the contents of the sample well for sufficient time and at sufficient temperature to allow for the formation of a fluorescent enzyme product should the enzyme be present in said red blood sample; (c) precipitating the hemoglobin; and (d) measuring the fluorescence of any fluorescent enzyme product formed in the sample well, directly from that sample well.

As used herein, the term "fluorescent enzyme product" shall include any fluorescent natural or artificial product of the catalytic action of the target enzyme. An example of a natural enzyme product is the NADH/NADPH formed by action of the GALT enzyme coupled sequence. An example of a fluorescent artificial enzyme product is the fluorescent product generated when a marker molecule is hydrolyzed or otherwise cleaved from an artificial substrate (e.g. 6-aminoquinoline is formed by the action of biotinidase on biotinyl-6-aminoquinoline).

Generally, the red blood sample will be in a form selected from the group consisting of whole blood, washed red blood cells, a hemolysate made from red blood cells, and dried whole blood on a physical support.

Examples of the buffer used in accordance with the present invention may be any non-interfering buffer appropriate for use in the aqueous assay of biological materials, such as phosphate, tris(hydroxyethyl)aminomethane, N-2-hydroxyethylpiperazine-N'-2-ethanesulfonic acid, N-ethylmorpholine, 5,5'-diethylbarbituric acid, N-2-hydroxyethylpiperazine-propanesulfonic acid, glycine, and mixtures thereof.

Hemoglobin may be precipitated through any known, non-interfering means or reagent, such as by the addition of ethanol.

It is preferred that the formation of the fluorescent enzyme product be halted prior to step (d). This may be done by any non-interfering means or reagent, such as by the application of heat, dilution, change of pH and/or the addition of an organic solvent. It is further preferred that the hemoglobin is precipitated and the formation of the fluorescent enzyme product be halted substantially simultaneously and prior to step (d).

Other reagents may be used in the assay mixture in accordance with the present invention, such as lysing reagents, surfactants, EDTA, dithiothreitol, metal cations (e.g. magnesium), enzymes, proteins, anti-microbial agents and enzyme stabilizers.

Where the sample is dried on a physical support, which is preferred, such support may be any suitable physical support for use in the handling of biological samples, such as filter paper. Where a physical support is used, it is preferred that the hemoglobin be precipitated onto the physical support prior to measuring the fluorescence of the fluorescent product directly from said sample well. The physical support will typically rest at the bottom of the sample well and, because fluorescence readings are typically taken from above, any interference from the reflectivity of the physical support will be substantially reduced, if not eliminated, by precipitation of the hemoglobin over or otherwise onto the physical support. This feature of the present invention is important, as it is typical to use filter paper spots as physical supports for blood samples (particularly from newborns). This is done for convenience (particularly when a large number of small samples are sent to testing labs) and to stabilize the blood sample during transport.

The present invention also includes a method for assaying the activity of an enzyme in a red blood target sample and comparing this activity to that of an enzyme-deficient red blood control sample, where both sample and control contain hemoglobin. This method comprises the general steps: (a) assaying the activity of the target enzyme both in a red blood target sample and in a red blood control sample comprising non-human mammal blood, in separate sample wells (each of the sample wells contain the respective samples and: (1) at least one substrate of the enzyme, (2) water, and (3) a buffer); (b) incubating the contents of each of the sample wells for sufficient time and at sufficient temperature to allow for the formation of a fluorescent enzyme product should the enzyme be present in the samples; (c) precipitating said hemoglobin in each of the sample wells; (d) measuring the fluorescence of any fluorescent enzyme product formed in each of the sample wells, respectively, directly from each of the sample wells; and (e) comparing the fluorescence of any fluorescent enzyme product formed in the red blood target sample well to the fluorescence of any fluorescent enzyme product formed in the red blood control sample well.

It is preferred that the red blood target sample and the red blood control sample be placed in the respective sample wells on a physical support, and that the hemoglobin be precipitated onto the physical support in step (c).

It is preferred that the enzyme-deficient red blood control sample comprise a non-human mammal blood selected from the group consisting of horse blood and sheep blood.

With respect to an assay for GALT activity, the method of the present invention, in broadest terms, comprises the steps of: (1) placing the following in a sample well: (a) a red blood sample; (b) galactose-1-phosphate; (c) uridine diphosphoglucose; (d) a substance selected from the group consisting of NAD and NADP; (e) water; and (f) a buffer adapted to maintain the pH within a range of from about 7.0 to about 8.5; (2) incubating the contents of the sample well for sufficient time and at sufficient temperature to allow for the formation of a substance selected from the group consisting of NADH and NADPH should galactose-1-phosphate uridyl transferase be present in said red blood sample; (3) precipitating the hemoglobin; and (4) measuring the fluorescence of any NADPH formed in the sample well, directly from said sample well.

Hemoglobin may be precipitated through any known, non-interfering means or reagent, such as by the addition of ethanol.

It is preferred that the formation of NADH/NADPH be halted prior to step (4). This may be done by any non-interfering means or reagent, such as by the application of heat, dilution, change of pH and/or the addition of an organic solvent. It is also preferred that the hemoglobin be precipitated and the formation of NADPH be halted substantially simultaneously and prior to step (4).

Other reagents may be used in the assay mixture in accordance with the present invention, such as lysing reagents, surfactants, EDTA, dithiothreitol, metal cations (i.e. magnesium), enzymes, proteins, anti-microbial agents and enzyme stabilizers.

Where the sample is dried on a physical support, such support may be any suitable physical support for use in the handling of biological samples, such as filter paper. Where a physical support is used, it is preferred that the hemoglobin be precipitated over or otherwise onto the physical support prior to measuring the fluorescence of the fluorescent product directly from said sample well.

In this invention, the Beutler and Baluda GALT screening assay has been adapted to a single reaction vessel, such as in a microtiter plate assay.

The Beutler and Baluda GALT assay has been adapted to a microtiter plate format using fluorescence readout. Disks (3 mm) punched from dried blood spots are incubated for three hours at 37° C. with a modified Beutler reagent in a black 96-well microtiter plate. Proteins, including hemoglobin, are precipitated by the addition of ethanol. The resulting precipitate is allowed to settle to the bottom of the well. The precipitate functions to cover the paper disk, which may affect the fluorescence reading. The microtiter plate is read with a fluorescent plate reader. Although hemoglobin from the sample quenches about 80% of the fluorescence of the NADPH product, there is a significant difference between the relative fluorescence of typical normal and deficient samples.

While the present assay may not be precisely quantitative because of hemoglobin interference, it has been found that increased GALT activity from more sample is nearly balanced by the quenching effect of hemoglobin.

The most common sample collection method used for newborn screening in the U.S. is filter paper dried blood spots (Guthrie cards). Typically, blood from a heel prick is blotted onto filter paper (Schleicher & Schuell #903, Keene, N.H.) and allowed to dry for several hours. Usually, samples are collected before the baby leaves the hospital. Other types of sample collection methods have been used to obtain blood. Because GALT activity is associated with the red blood cell, blood but not serum or plasma is the sample of choice. Blood can be collected in capillary tubes. Anticoagulated whole blood or washed blood cells may also be used.

The reagent used for measuring GALT activity in blood may consist of the following primary components: GAL-1-P, UDPG, and NADP. These are the same components used by Beutler and Baluda and others in the literature since this procedure was published. GAL-1-P and UDPG are substrates for GALT. The NADP acts as a substrate for G-6-PDH and 6-PGD. NAD also acts as a substrate for G-6-PDH and 6-PGD and could be substituted for NADP.

The reaction is pH dependent, so a buffer is required. Buffers have been used to control the pH in the range of about 7.6 to about 8.0. Any buffer that controls the pH in the desired range and does not substantially affect GALT activity could be used in the reagent. Examples include phosphate buffers, N-2-hydroxyethylpiperazine-N'-2-ethanesulfonic acid (HEPES), N-ethylmorpholine, 5,5-diethylbarbituric acid, N-2-hydroxyethylpiperazine-propanesulfonic acid (HEPPS), and Tris-acetate and glycine. Of course, the invention is not limited to the use of these specific buffers.

Other components can be added to the reaction mixture to enhance enzymatic activity. These include lysing reagents, surfactants, EDTA, DTT, metal cations (e.g. magnesium ($Mg^{+2}$)), enzymes, proteins, anti-microbial agents, and enzyme stabilizers. Lysing reagents function to burst intact red blood cells so that the enzymes of interest are released into solution. Examples include saponin, digitonin, or any suitable surfactant. Because lysing reagents usually have some surfactant properties, they also serve to aid in the extraction of the sample from the paper. EDTA, DTT and magnesium have all been reported as enhancers for the Beutler assay. They function to increase or restore the enzymatic activity (i.e. lost due to heating) in the sample for not only GALT but also for PGM, G-6PDH, and/or 6-PGD. Alternatively, PGM, G-6PDH, and/or 6-PGD can be added to the reagent. Thus, if the sample is deficient in one of these enzymes, the reagent can still detect GALT. Proteins and stabilizers (i.e. sugars, polymers) could also be added to stabilize the reagent. Anti-microbial agents could also be added to prevent microbial growth during storage of the reagent. The latter considerations are important if the reagent is to be stored and shipped, perhaps as part of a kit.

Incubations are typically performed at 37° C., which increases GALT activity compared to room temperature. However, any incubation temperature could be used, as long as GALT activity of normal and deficient samples can be differentiated. The reaction vessel (in this case a microtiter plate) can be shaken or rocked during the incubation. This serves to aid elution of sample from the spot and to keep all reaction components well-mixed. There are many types of microtiter plates available. An opaque plate functions to prevent well-to-well leakage of fluorescence during plate reading. Both black and white plates are currently available from several manufacturers (i.e. Labsystems OY, Helsinki, Finland). Standard clear plates could also be used if well-to-well interference is not found.

The reaction can be read with or without stopping by a reagent which prevents further enzymatic activity. It has been found that there are several advantages to stopping the reaction. Precipitating proteins in the reaction mixture, at the same time as stopping, also has several advantages: (1)

lessening the interference due to hemoglobin; (2) being able to read the plate at a convenient time, rather than at a particular time; (3) the results are more reproducible; (4) the eluted paper spot, being preferrably at the bottom of the plate and covered with precipitated protein, does not affect the fluorescence reading. There are many ways to stop the reaction and precipitate proteins. Heat denaturation may be used. Organic solvents, such as ethanol, methanol, and acetone, either by themselves, mixed together or mixed with water or buffer could be used. Frazier, Clemons, and Kirkman used a holding solution which acted to dilute the reaction mixture so that further enzymatic activity was greatly reduced. Other possible means of stopping the reaction include adjusting the pH with acid or base so that the reaction is stopped or slowed and/or the protein precipitates; and adding a heavy metal salt (e.g. zinc chloride) to precipitate proteins. After the reaction has been stopped by precipitation of proteins, it is advantageous for the precipitate to settle prior to reading. This can be done by simply allowing the plate to sit for about 30 minutes or by centrifugation of the plate. Settling removes turbidity from the assay mixture so that consistent fluorescence readings can be made.

The plate can be read in any of a number of fluorescent plate readers. These readers have a light source which is directed from above the plate and the resultant fluorescence is detected by a detector positioned either directly above the plate or at an angle above the plate. Examples of such readers include: Labsystems Fluoroskan, Corona Electric Fluorescent Plate Reader (Tokyo, Japan), IDEXX FCA (IDEXX Laboratories, Westbrook, Me.), Cambridge Technology 7610 Microplate Fluorometer (Watertown, Mass.), Dynatech MicroFLUOR Reader (Chantilly, Va.), and Millipore CytoFluor Fluorescence Plate Reader (Bedford, Mass.).

Another aspect of the method of the invention is the use of an animal blood control in the GALT assay method. It has been found that animal blood samples, such as horse and sheep blood, make particularly good control samples because they are naturally deficient or lacking in the GALT enzyme.

When used in a biotinidase assay, the present invention is a method for assaying biotinidase activity in a red blood sample. The method comprises the steps: (1) placing the following in a sample well: (a) a red blood sample; (b) biotin labeled with a marker molecule; (c) water; and (d) a buffer adapted to maintain the pH within a range of from about 6.0 to about 7.5; (2) incubating the contents of the sample well for sufficient time and at sufficient temperature to allow for the formation of a fluorescent enzyme product should biotinidase be present in the red blood sample; (3) precipitating the hemoglobin; and (4) measuring the fluorescence of any the fluorescent enzyme product formed in the sample well, directly from the sample well.

The typical sources of red blood samples, the typical buffers, the precipitating agents, the steps pertaining to the halting of the enzyme reaction and the precipitation of the hemoglobin, and the additional components may be as described above with respect to the GALT assay.

It is also preferred that the sample(s) be placed on a physical support as described above.

The biotinidase assay may also be performed as an assay against a known or calibrated standard similar to that described above with respect to the GALT assay. Non-human mammalian blood however cannot be used as a biotinidase-deficient control. Rather, other control samples, such as known standards, must be used.

The preferred embodiment of the present invention, used in a method for assaying biotinidase activity, in broadest terms, comprises the steps: (1) placing the following in the sample well: (a) a red blood sample; (b) biotinyl-6-aminoquinoline; (c) dithiothreitol; (d) water; and (e) a buffer adapted to maintain the pH within a range of from about 6.0 to 7.5; (2) incubating the contents of the sample well for sufficient time and temperature to allow the formation of 6-aminoquinoline; (3) precipitating the hemoglobin; and (4) measuring the fluorescence of any 6-aminoquinoline formed in the sample well, directly from said sample well.

Examples of the buffer used in accordance with the present invention may be any noninterfering buffer appropriate for use in the aqueous assay of biological materials, such as potassium phosphate buffer.

Hemoglobin may be precipitated through any known, non-interfering means or reagent, such as by the addition of ethanol.

Other reagents may be used in the assay mixture in accordance with the present invention, such as enzymes, proteins, anti-microbial agents and stabilizers.

When the sample is dried on a physical support, such support may be any suitable physical support for use in the handling of biological samples, such as filter paper. Where a physical support is used, it is preferred that the hemoglobin be precipitated on top of or otherwise onto the physical support prior to measuring the fluorescence product directly from said sample well.

In this invention, the Pitkanen and Tuuminen assay has been adapted so that dried-blood disks can be used. It is automatable and practical.

The present method, and others similar to it, can be used for routine neonatal screening for any enzyme and in other applications, particularly where convenience and accuracy are desired from minimal sampling volume.

The major advantages of the present invention in its many embodiments over previous technology include:

1. The assay can be run in a single analysis vessel (microtiter plate).
2. The assay is designed to work on blood spots dried on filter paper.
3. The sample support need not be removed prior to analysis.
4. Only one reading is necessary.
5. Increases in enzyme activity due to the presence of more sample is nearly balanced by the quenching effect of hemoglobin.
6. Enzyme deficient controls can be made from horse or other animal blood, naturally deficient or lacking in the target enzyme.

Figure 1:
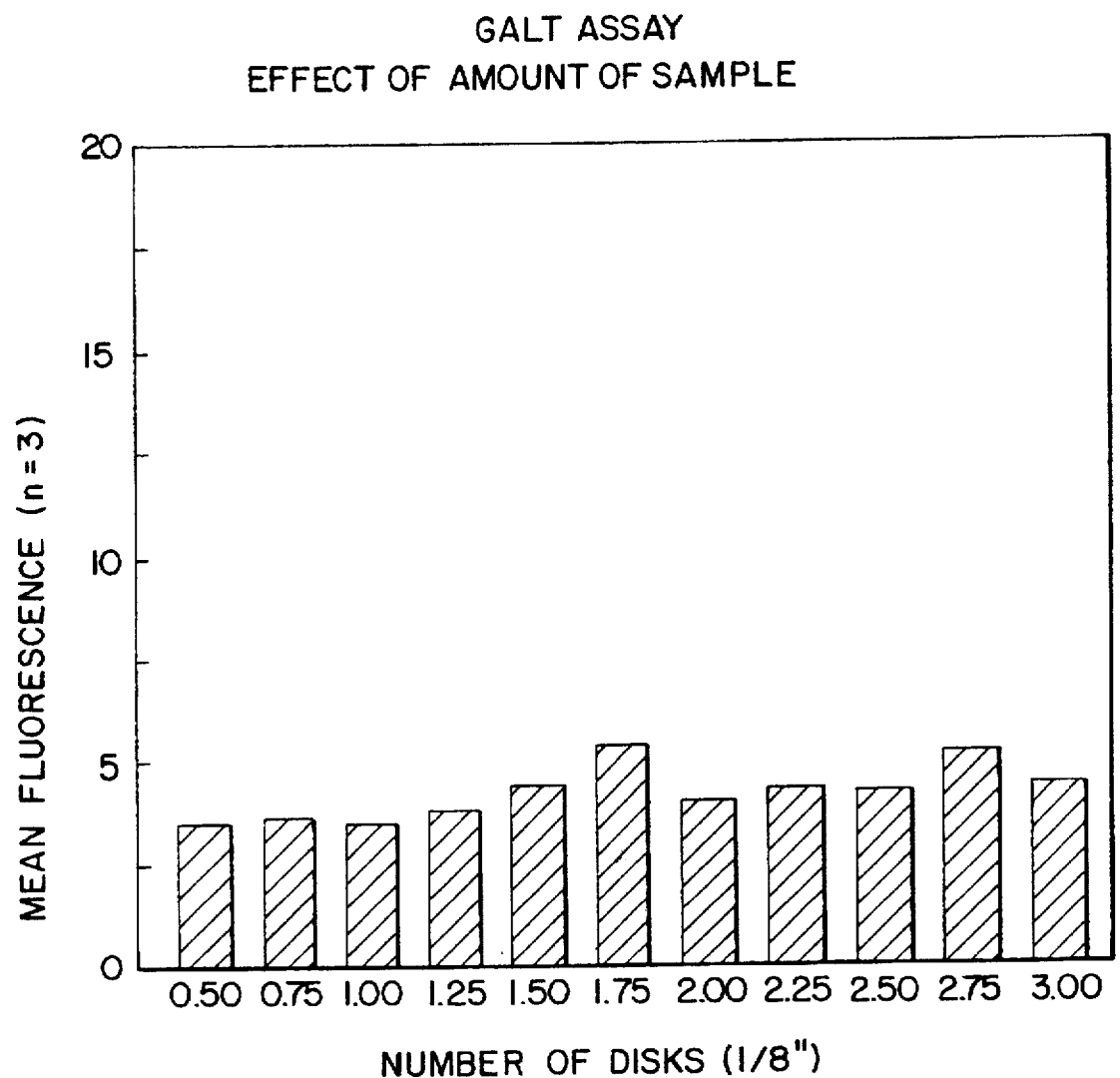
FIG. 1 is a graph showing the results of the experiment described in Example 2A.

DETAILED DESCRIPTION OF THE PREFERRED EMBODIMENTS AND BEST MODE FOR CARRYING OUT THE INVENTION

The following presents several examples of the present invention. The best mode for carrying out the invention for an assay for GALT is considered to be the assay as detailed in Example 1. The best mode for carrying out the invention for an assay for biotinidase is considered to be the assay as detailed in Example 8.

EXAMPLES

Example 1

A reagent consisting of 0.25 mol/L Tris, 0.192 g/L magnesium sulfate, 0.0327 g/L EDTA, 5.27 g/L GAL-1-P, 2.64 g/L UDPG, 4.64 g/L NADP, and 4.64 g/L DTT, adjusted to pH 7.98 with hydrochloric acid was mixed. Punches (1/8") from blood dried on filter paper were placed in the wells of a black microtiter plate (Labsystems). GALT reagent (100 µL/well) was added to each well. The plate was placed in a Labsystems iEMS Incubator/shaker and it was incubated at 37° C. for three hours with shaking (400 RPM). Absolute EtOH (250 µL/well) was added and the plate was shaken for 1 minute. The plate was then allowed to sit for 30 minutes at room temperature and read on a Labsystems Fluoroskan reader (excitation 355 nm, emission 460 nm). The resulting fluorescence values were:

| SAMPLE | n | MEAN FLUORESCENCE | STANDARD DEVIATION |
|---|---|---|---|
| NORMAL #1 | 8 | 8.33 | 0.53 |
| DEFICIENT | 8 | 1.17 | 0.14 |
| NORMAL #2 | 8 | 5.86 | 0.53 |
| NORMAL #3 | 8 | 15.7 | 2.18 |
| NORMAL #4 | 8 | 14.4 | 0.40 |

Normal samples 3 and 4 were fresh; samples 1 and 2 were older. This Example demonstrates that: (1) there is a clear distinction between normal and deficient samples; (2) older samples loose enzymatic activity with time; (3) the precision of the assay is good —CVs are less than 15%.

Example 2

This experiment demonstrates the quenching effect of hemoglobin on the NADPH product. NADPH (4.7 mg/10 mL) was dissolved in 0.25 mol/L Tris, 0.192 g/L magnesium sulfate, 0.0327 g/L EDTA buffer, adjusted to pH 8.0 with HCl. Blood spots were punched into the wells of black microtiter plates. Some wells had no spots, some had one 3 mm spot, some had one 3 mm and one 1.5 mm spot (1.25 spots—by volume). The buffered NADPH solution (100 µL) was added to each well (Buffer only was added to some wells as a control). The plate was incubated, read on the Fluoroskan, and the stop reagent was added as in Example 1. The plate was then read in the Fluoroskan. The resulting values were:

| SAMPLE | NO. OF SPOTS | FLUORESCENCE NO EtOH | FLUORESCENCE WITH EtOH |
|---|---|---|---|
| NO SPOT | 0 | 32.2 | 91.3 |
| NORMAL #5 | 1 | 8.5 | 19.4 |
| NORMAL #5 | 1.25 | 3.1 | 15.6 |
| DEFICIENT | 1 | 11.5 | 19.8 |
| DEFICIENT | 1.25 | 7.6 | 14.9 |
| NORMAL #6 | 1 | 6.9 | 13.7 |
| NORMAL #6 | 1.25 | 5.6 | 12.3 |

Before the EtOH was added, the white disks could be seen on the bottom of the wells. This experiment showed that: (1) the EtOH enhances fluorescence and hides the extracted paper disk; (2) hemoglobin quenching is about 80% for a typical spot; (3) a 25% increase in the amount of sample causes an average 19% drop in fluorescence (4) the quenching effect of hemoglobin is reduced in the stopped reaction; (5) the hemoglobin quenching effect is more reproducible in the stopped reaction, possibly because the disk is hidden.

Example 2A

Because the effect of hemoglobin quenching is so extreme, the effect of adding more sample was examined. This experiment demonstrates that the quenching effect of hemoglobin is nearly balanced by the increase in GALT activity due to the increase in sample size. The GALT assay in Example 1 was repeated on three samples with various disk sample loads (0.5 to 3.0 1/8" disks, n =11 different sample loads). The results are shown in FIG. 1. The various fractions of disks were loaded as combinations of 1/8" and 1/16" disks. The blood volume in one 1/8" disk is equivalent to four (4) 1/16" disks. It was found that the measured amount of GALT activity was nearly independent of sample mount.

Example 3

The assay was run as in Example 1 except that various stop solutions were used. These included absolute ethanol, methanol, acetone, or a solution of 40% ethanol and 6% zinc sulfate in water (EtOH/Zn). The resulting fluorescence values were:

| SAMPLE | n | MEAN FLUORESCENCE | | | |
|---|---|---|---|---|---|
| | | EtOH | MeOH | ACETONE | EtOH/Zn |
| NORMAL #7 | 2 | 11.7 | 15.8 | 16.8 | 7.76 |
| NORMAL #8 | 2 | 10.4 | 10.7 | 13.5 | 5.83 |
| DEFICIENT | 4 | 1.58 | 1.85 | 1.89 | 1.85 |
| NORMAL #9 | 4 | 10.6 | 10.7 | 16.0 | 5.58 |
| NORMAL #10 | 2 | 5.24 | 6.11 | 7.11 | 5.09 |

This experiment showed that any one of these stop reagents could be used in this assay. Note that the Normal #10 sample was over one year old, but still had enough activity to differentiate it from the deficient sample.

Example 4

The experiment of Example 3 was repeated. Instead of allowing the plate to settle after the stop reagents were added, the plate was centrifuged for eight minutes at 3500 RPM in an IEC Centra MP4 (Needham Heights, Mass.) centrifuge. The resulting fluorescence values were:

| SAMPLE | n | MEAN FLUORESCENCE | | | |
|---|---|---|---|---|---|
| | | EtOH | MeOH | ACETONE | EtOH/Zn |
| NORMAL #7 | 2 | 10.3 | 20.1 | 12.0 | 7.31 |
| NORMAL #8 | 2 | 9.77 | 18.5 | 8.66 | 5.89 |
| DEFICIENT | 4 | 1.52 | 2.09 | 1.69 | 1.94 |
| NORMAL #9 | 4 | 10.6 | 21.0 | 9.73 | 5.49 |
| NORMAL #10 | 2 | 5.08 | 8.10 | 5.20 | 4.72 |

The acetone-containing wells evaporated appreciably during centrifugation. This experiment showed that any one of these solvents could be used in the centrifugation-modified assay.

Example 5

The experiment in Example 1 was repeated except that glucose-1-phosphate (1.7 mg/mL of reagent) was added to the reagent. The normal reagent was run as a control. This was an attempt to see if deficient samples have acceptable levels of PGM, G-6-PDH and 6-PGD (these enzymes are necessary for NADPH formation and are supplied by the blood sample). If these enzymes are deficient or have been denatured (i.e. by heat), a sample may appear deficient for GALT, even though GALT activity is present. Adult horse blood is naturally deficient in GALT, but still has active PGM, G-6-PDH, and 6-PGD enzymes. Adult sheep blood was also tested. The resulting fluorescence values were:

| SAMPLE | n | MEAN FLUORESCENCE ± SD | |
|---|---|---|---|
| | | NO G-1-P | WITH G-1-P |
| DEFICIENT | 2 | 1.10 ± 0.07 | 18.6 ± 0.23 |
| HORSE BLOOD | 2 | 2.07 ± 0.05 | 19.5 ± 0.12 |
| NORMAL #11 | 10 | 3.48 ± 0.16 | 17.6 ± 0.77 |
| NORMAL #12–19 | 16 | 2.61 ± 0.49 | 17.3 ± 2.2 |
| SHEEP BLOOD | 8 | 0.81 ± 0.04 | 0.94 ± 0.09 |
| NORMAL #20 | 8 | 4.92 ± 0.03 | 16.7 ± 0.48 |

This assay shows that: (1) horse blood can be used as a GALT deficient control; (2) it appears that our sample of adult sheep blood is deficient in GALT, PGM, G-6-PDH, and/or 6-PGD activity; (3) a GALT deficient sample still had active PGM, G-6-PDH, and 6-PGD enzymes; (4) older samples (i.e. Normal #11) with decreased GALT activity still have functioning PGM, G-6-PDH, and 6-PGD enzymes; (5) red cell PGM, G-6-PDH, and/or 6-PGD activity can be checked using this method.

Example 6

The experiment in Example 1 was repeated except three different reagents were used. The reagents were adjusted to pH 7.0, pH 8.0 and pH 8.7.

| SAMPLE | n | RELATIVE FLUORESCENCE | | |
|---|---|---|---|---|
| | | pH 7.0 | pH 8.0 | pH 8.7 |
| NORMAL #21 | 2 | 2.78 | 3.79 | 3.00 |
| DEFICIENT | 2 | 0.94 | 1.20 | 1.10 |
| NORMAL #22 | 2 | 3.34 | 5.67 | 3.92 |
| NORMAL #23 | 2 | 2.73 | 5.05 | 2.79 |
| NORMAL #24 | 2 | 2.73 | 3.77 | 2.45 |
| NORMAL #25 | 2 | 2.81 | 3.85 | 3.24 |

Normal samples 22 and 23 were fresh; samples 24 and 25 were older. This Example demonstrates that: (1) there is a clear distinction between normal and deficient samples over the entire range of tested pH; (2) older samples can be distinguished from deficient samples over the entire range of tested pH.

Example 7

The experiment in Example 1 was repeated except different sample types were used. Because a ⅛" punch contains about 3 μL of blood, 3 μL of liquid sample was placed in some of the wells instead of a punched sample. Whole blood was collected in heparin tubes from three adult volunteers. Blood from a finger-stick was obtained in a capillary tube and immediately pipetted into the microtiter plate before clotting occurred. Washed blood was obtained by washing a whole blood sample four times with isotonic saline. A hemolyzed sample was obtained by addition of one volume of water to one volume of packed red cells.

| SAMPLE | n | RELATIVE FLUORESCENCE |
|---|---|---|
| NORMAL #21 SPOT | 2 | 3.79 |
| DEFICIENT SPOT | 2 | 1.20 |
| WHOLE BLOOD #1 | 3 | 6.22 |
| WHOLE BLOOD #2 | 3 | 4.74 |
| WHOLE BLOOD #3 | 3 | 11.5 |
| FINGER PRICK | 3 | 8.10 |
| WASHED BLOOD | 3 | 6.17 |
| HEMOLYSATE | 3 | 6.78 |

This example demonstrates that GALT activity can be measured in the following liquid blood sample types: whole blood, capillary blood, washed cells and hemolysates. The following references are hereby incorporated herein by reference:

1. Beutler E, Baluda, M: A simple spot screening test for galactosemia *J Lab Clin Med* 68:137 (1966).
2. Beutler E: Galactosemia: screening and diagnosis. *Clin. Biochem.* 24:293 (1991).
3. Sigma Diagnostics: Galactose-1-phosphate uridyl transferase deficiency. Procedure No. 195 (1985).
4. Berry H K: Reagent that restores galactose-1-phosphate uridyltransferase activity in dry blood spots. *Clin. Chem.* 33:1471 (1987).
5. Hochella N J and Hill J B: Fluorometric screening procedure for galactosemia utilizing the autoanalyzer. *Clin. Chem.* 15:949 (1969).
6. Pesce M A, Bodourian S H, Harris R C, Nicholson J F: Enzymatic micromethod for measuring galactose-1-phosphate uridyltransferase activity in human erythrocytes. *Clin. Chem.* 23:1711 (1977).
7. Greenberg C R, Dilling L A, Thompson R, Ford J D, Seargeant L E, Haworth J C: Newborn screening for galactosemia: a new method used in Manitoba. *Pediatrics* 84:331 (1989).
8. Yamaguchi A, Fukushi M, Mizushima Y, Shimizu Y, Takasugi N, Arashima S, Ohyanagi K: Microassay for screening newborns for galactosemia with the use of a fluorometric microplate reader. *Clin. Chem.* 35:1962 (1989).
9. Frazier D M, Clemons E H, Kirkman H N: Minimizing false positive diagnoses in newborn screening for galactosemia. *Biochem. Med. Metabol. Biol.* 48:199 (1992).

The best mode for carrying out the invention is the assay as a biotinidase assay is given in Example 8.

Example 8

A reagent consisting of 40.2 μmol/L Biotinyl-6-Amidoquinoline (BAQ), 1.5 mmol/L dithiothreitol, 6 g/L sucrose in 0.15M Potassium Phosphate buffer, pH 7.0 was mixed. Punches (⅛" disks) from blood dried on filter paper were placed in the wells of a black microtiter plate (Labsystems). BAQ reagent (100 μL/well) was added to each well. The plate was placed in a Labsystems iEMS Incubator/shaker and it was incubated at 37° C. for 17 hours without shaking. Absolute ethanol (200 μL/well) was added and the plate was shaken for 1 minute. The plate was then allowed to sit for 30 minutes at room temperature and read on a Labsystems Fluoroskan reader (excitation 355 nm, emission 544 nm). The resulting fluorescence values were:

| SAMPLE | n | MEAN FLUORESCENCE | STANDARD DEVIATION |
|---|---|---|---|
| DEFICIENT #1 | 8 | 0.5 | 0.2 |
| DEFICIENT #2 | 8 | 0.4 | 0.1 |
| NORMAL #1 | 8 | 17.2 | 0.4 |
| NORMAL #2 | 8 | 16.4 | 0.5 |
| NORMAL #3 | 8 | 14.4 | 1.0 |
| 16 PATIENTS | 16 | 9.3 | 1.8 |

This example demonstrates that: (1) there is a clear distinction between normal and deficient samples; (2) the normal samples, which were fresh (as compared to the 16 patient samples), exhibited higher enzymatic activity, i.e older samples loose enzymatic activity with time; (3) the precision of the assay is good—CVs are less than 15% for the normal samples; (4) this general method can be used to assay serum enzymes as well as red blood cell associated enzymes (as shown in the other examples) in hemoglobin containing samples.

The following references are hereby incorporated herein by reference:

1. Wolf B, Heard G S: Screening for biotinidase deficiency in newborns: worldwide experience. *Pediatrics* 85:512 (1990).
2. Dunkel G, Scriver C R, Clow C L, Melancon S, Lemieux B, Grenier A, Laberge C: Prospective ascertainment of complete and partial serum biotinidase deficiency in the newborn. *J. Inher. Metab. Dis.* 12:131 (1989).
3. Lawler M G, Frederick D L, Rodriguez-Anza S, Wolf B, Levy H L: Newborn screening for biotinidase deficiency: pilot study and follow-up of identified cases. *Screening* 1:37 (1992).
4. Pitkanen L, Tuuminen T: A quantitative fluorometric micromethod used for the neonatal screening of biotinidase deficiency in Finland. *Screening* 1:185 (1992).
5. Wolf B, Heard G S. Disorders of biotin metabolism: In Scriver C R, Beaudet A L, Sly W S, Valle D (eds); "The Metabolic Basis of Inherited Disease." New York: McGraw-Hill: 2083 (1989).
6. Dove Pettit D A, Wolf B. Quantitative Colorimetric Assay of Biotinidase Activity. "Techniques in Diagnostic Human Biochemical Genetics: A Laboratory Manual." Wiley-Liss Inc.: 56(1991).
7. Wolf B, Heard G S, Weissbecker K A, Secor McVoy J R, Crier R E, Leshner R T: Biotinidase deficiency: Initial clinical features and rapid diagnosis, *Ann. Neurol.* 18:614 (1989).
8. Wolf B, Grier R E, Alien R J, Goodman S I, Kien C L, Parker W D, Howell D M, Hurst D L: Phenotypic variation in biotinidase deficiency. *J. Pediatr.* 103:233 (1983).
9. Wastell H, Dale G, Bartlett K: A Sensitive Fluorimetric Rate Assay for Biotinidase Using a New Derivative of Biotin, Biotnyl-6-aminoquinoline. *Anal. Biochem.* 140:69 (1984).
10. Knappe J, Brummer W, Biederbick K: Reinigung und eigenschaften der Biotinidase aus Schweinenieren und Lactobacillus casei. *Biochem. Z.* 338:599 (1963).
11. Hayakawa K, Oizumi J: Determination of biotinidase activity by liquid chromatography with fluorimetric detection. *J. Chromatogr.* 383:148(1986).
12. Weiner D L, Grier R E, Wolf B: A bioassay for determining biotinidase activity and for discriminating biocytin from biotin using holocarboxylase synthetase-deficient cultured fibroblasts. *J. Inherited Metab. Dis.* 8(Supple 2):101 (1985).
13. Thoma R W, Peterson W H: The enzymatic degradation of soluble bound biotin. *J. Biol. Chem.* 210:569 (1954).
14. Wright L D, Driscoll C A, Boger W P: Biocytinase, an enzyme concerned with hydrolyric cleavage of biocytin. *Proc. Soc. Exp. Biol. Med* 86:335(1954).
15. Baker H, DeAngelis B, Frank O: Plasma biotinidase assay using the protozoan *Ochromonas danica*. *Nutr. Rep. Int.* 39:243(1989).
16. Thuy L P Zielinska B, Sweetman L, Nyhan W L: Determination of biotinidase activity in human plasma using [$^{14}$C]-biocytin as substrate. *Ann. N.Y. Acad Sci.* 447:434 (1985).
17. Wolf B, Heard G S, Jefferson L, Proud V K, Nance W E, Weissbecker K A: Clinical findings in four children with biotinidase deficiency detected through a statewide neonatal screening program. *N. Engl. J. Med.* 313:16(1985).

In view of the foregoing disclosure of the present invention and from its practice, it will be within the ability of one of ordinary skill in the art to make alterations and substitutions to the present invention, such as through the use of equivalent materials and the combination of process steps, to practice the present invention without departing from its scope as reflected in the appended claims.

What is claimed is:

1. A method for assaying biotinidase activity in a red blood sample, said sample containing hemoglobin, said method comprising the steps:
   (a) placing the following contents in a sample well:
      (i) a red blood sample;
      (ii) biotin labeled with a marker molecule said labeled biotin able to react to form a fluorescent enzyme product;
      (iii) water; and
      (iv) a buffer adapted to maintain the pH within a range of from about 7.0 to about 8.5;
   (b) incubating said contents of said sample well for sufficient time and at sufficient temperature to allow for the formation of said fluorescent enzyme product should said biotinidase be present in said red blood sample; followed by
   (c) precipitating said hemoglobin; and
   (d) measuring the fluorescence of any said fluorescent enzyme product formed in said sample well, directly from said sample well.

2. A method according to claim 1 wherein said red blood sample is placed in said sample well in a form selected from the group consisting of whole blood, washed red blood cells, a hemolysate made from red blood cells, and dried whole blood on a physical support.

3. A method according to claim 1 wherein said buffer is selected from the group consisting of phosphate, tris (hydroxyethyl)aminomethane, N-2-hydroxyethylpiperazine-N'-2-ethanesulphonic acid, N-ethylmorpholine, 5,5'-diethylbarbituric acid, N-2-hydroxyethylpiperazine-propanesulphonic acid, glycine, and mixtures thereof.

4. A method according to claim 1 wherein said hemoglobin is precipitated by addition of ethanol.

5. A method according to claim 1 wherein the formation of said fluorescent enzyme product is halted prior to step (d).

6. A method according to claim 5 wherein the formation of said fluorescent enzyme product is halted by a method selected from the group consisting of the application of heat, dilution, change of pH and addition of an organic solvent.

7. A method according to claim 5 wherein said hemoglobin is precipitated and the formation of said fluorescent enzyme product is halted substantially simultaneously and prior to step (d).

8. A method according to claim 1 wherein said sample well is also provided with at least one component selected from the group consisting of lysing reagents, surfactants, ethylenediaminetetraacetic acid, dithiothreitol, magnesium, enzymes, proteins, anti-microbial agents and enzyme stabilizers.

9. A method for assaying biotinidase activity in a red blood sample, said sample containing hemoglobin, said method comprising the steps:
   (a) placing the following in a sample well:
      (i) a dried red blood sample on a physical support;
      (ii) biotin labeled with a marker molecule said labeled biotin able to react to form a fluorescent enzyme product;
      (iii) water; and
      (iv) a buffer adapted to maintain the pH within a range of from about 6.0 to about 7.5;
   (b) incubating the contents of said sample well for sufficient time and at sufficient temperature to allow for the formation of a fluorescent enzyme product should said biotinidase be present in said red blood sample; followed by (c) precipitating said hemoglobin onto said physical support; and (d) measuring the fluorescence issuing from any said Fluorescent enzyme product formed in said sample well, directly from said sample well.

10. A method according to claim 9 wherein said sample is placed in said sample well in a form of dried whole blood on a physical support.

11. A method according to claim 9 wherein said physical support comprises filter paper.

12. A method according to claim 9 wherein said buffer is selected from the group consisting of phosphate, tris(hydroxyethyl)aminomethane, N-2-hydroxyethylpiperazine-N'-2-ethanesulphonic acid, N-ethylmorpholine, 5,5'-diethylbarbituric acid, N-2-hydroxyethylpiperazine-propanesulphonic acid, glycine, and mixtures thereof.

13. A method according to claim 9 wherein said hemoglobin is precipitated by addition of ethanol.

14. A method according to claim 9 wherein the formation of said fluorescent enzyme product is halted prior to step (d).

15. A method according to claim 14 wherein the formation of said fluorescent enzyme product is halted by a method selected from the group consisting of the application of heat, dilution, change of pH and addition of an organic solvent.

16. A method according to claim 14 wherein said hemoglobin is precipitated onto said physical support and the formation of said fluorescent enzyme product is halted substantially simultaneously and prior to step (d).

17. A method according to claim 9 wherein said sample well is also provided with at least one component selected from the group consisting of lysing reagents, surfactants, ethylenediaminetetraacetic acid, dithiothreitol, magnesium, enzymes, proteins, anti-microbial agents and enzyme stabilizers.

18. A method for assaying biotinidase activity in a red blood target sample and comparing same to that of a red blood control sample, said samples containing hemoglobin, said method comprising the steps:

(a) assaying biotinidase activity both in a red blood target sample and in a red blood control sample comprising non-human mammal blood, in separate sample wells, each of said sample wells containing contents comprising respective said samples and:
 (i) biotin labeled with a marker molecule said labeled biotin able to react to form a fluorescent enzyme product;
 (ii) water; and
 (iii) a buffer adapted to maintain the pH within a range of from about 6.0 to about 7.5;

(b) incubating said contents of each of said sample wells for sufficient time and at sufficient temperature to allow for the formation of a fluorescent enzyme product should said biotinidase be present in said samples; followed by (c) precipitating said hemoglobin in each of said sample wells; and (d) measuring the fluorescence of any said fluorescent enzyme product formed in each of said sample wells, respectively, directly from each of said sample wells;

(e) comparing the fluorescence of any said fluorescent enzyme product formed in said red blood target sample well to the fluorescence of any said fluorescent enzyme product formed in said red blood control sample well.

19. A method according to claim 18 wherein said red blood target sample and said red blood control sample are placed in said respective sample wells on a physical support, and wherein said hemoglobin is precipitated onto said physical support in step (c).

20. A method according to claim 18 wherein said red blood control sample comprises a non-human mammal blood selected from the group consisting of horse blood and sheep blood.

* * * * *

UNITED STATES PATENT AND TRADEMARK OFFICE
CERTIFICATE OF CORRECTION

PATENT NO. : 5,719,035

DATED : February 17, 1998

INVENTOR(S) : Rosenthal et al.

It is certified that error appears in the above-indentified patent and that said Letters Patent is hereby corrected as shown below:

In column 12, line 13, please delete the word "mount" and replace it with -- amount Signed and Sealed this Seventh Day of July, 1998

Attest:

BRUCE LEHMAN

Attesting Officer

Commissioner of Patents and Trademarks